United States Patent [19]

Yamagata et al.

[11] Patent Number: 4,741,009
[45] Date of Patent: Apr. 26, 1988

[54] X-RAY DIAGNOSTIC APPARATUS FOR ANALYZING SCATTERED X-RAYS BY USING X-RAY SHIELD MEMBER

[75] Inventors: Hitoshi Yamagata, Ootawara; Katsuya Kikuchi, Tochigi, both of Japan

[73] Assignee: Kabushiki Kaisha Toshiba, Kawasaki, Japan

[21] Appl. No.: 792,855

[22] Filed: Oct. 30, 1985

[30] Foreign Application Priority Data

Oct. 31, 1984 [JP] Japan ................ 59-229748

[51] Int. Cl.$^4$ ............... G21K 1/04; H05G 1/64
[52] U.S. Cl. .................. 378/99; 148/149; 148/154; 148/155
[58] Field of Search ............ 378/2, 7, 46, 83, 84, 378/85, 89, 87, 98, 99, 145, 149, 150, 154, 155, 148; 250/363 SH; 358/111

[56] References Cited

U.S. PATENT DOCUMENTS

| | | | |
|---|---|---|---|
| 4,399,457 | 8/1983 | Riederer et al. | 378/99 |
| 4,549,307 | 10/1985 | Macovski | 378/7 |
| 4,550,419 | 10/1985 | Aichinger et al. | 478/99 |
| 4,656,650 | 4/1987 | Kikuchi et al. | 378/7 |

*Primary Examiner*—Carolyn E. Fields
*Assistant Examiner*—Joseph A. Hynds
*Attorney, Agent, or Firm*—Finnegan, Henderson, Farabow, Garrett & Dunner

[57] ABSTRACT

An X-ray diagnostic apparatus analyzes scattered X-ray distribution from total X-ray transmission data by employing an X-ray shield member. One of plural X-ray shield members is selected based on the X-ray magnifying factor of a region of interest (ROI) in a patient. The scattered X-ray distribution $I_{sc}(x,y)$ over the entire X-ray projection area is calculated by utilizing a method of linear interpolation and the actually measured scattered X-ray components.

13 Claims, 10 Drawing Sheets

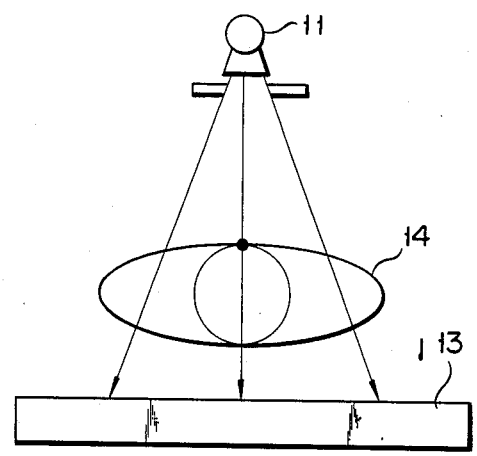
F I G. 3A
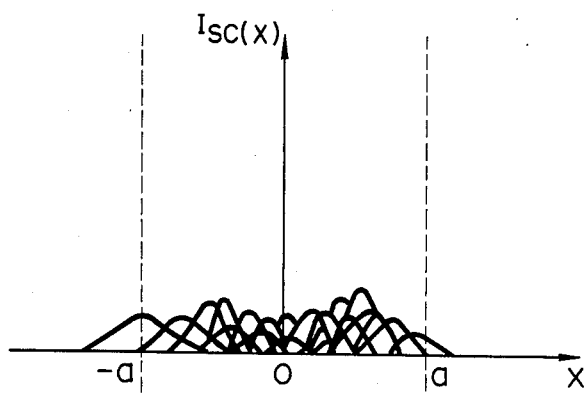
F I G. 3B
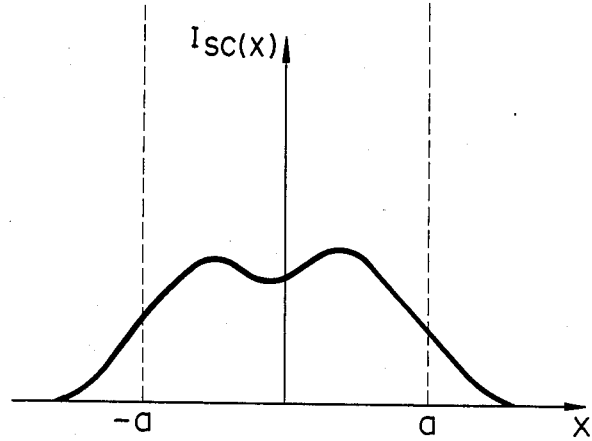
F I G. 3C

X-RAY DIAGNOSTIC APPARATUS FOR ANALYZING SCATTERED X-RAYS BY USING X-RAY SHIELD MEMBER

BACKGROUND OF THE INVENTION

1. Field of the Invention

This invention generally relates to an X-ray diagnostic apparatus in which a transmitted X-ray image of an object under examination, e.g., a patient, is available for diagnostic purposes, and more particularly, to an X-ray diagnostic apparatus by which visible X-ray images of the object can be obtained, based only upon primary X-rays, without any adverse influences caused by the scattered X-rays.

2. Description of Prior Art

Generally, in the X-ray diagnostic apparatus set forth in the preamble, X-rays incident on an X-ray detector through the object such as a patient contain not only primary X-rays but also X-rays which are scattered by the object under examination. The scattered X-rays constitute one of the major causes of deteriorated contrast and resolution in the transmitted X-ray image. This makes it necessary to eliminate an image component on the scattered X-rays from the transmitted X-ray image data as sensed and provided by the detector.

One of the approaches to eliminate the scattered X-ray component is to use a so-called "Buckey Blade" or an elimination grid for the scattered X-rays (referred to as a "grid"). This approach introduces a new problem in that there is a limit in the scattered X-ray elimination, because the grid itself may cause scattered X-rays therefrom.

The elimination of the scattered X-rays is very significant in the field of X-ray diagnosis for the reasons that it improves an image quality, such as contrast and resolution, and thus allows a logarithm conversion of primary X-rays image data, thereby obtaining an accurate attenuation quantity of X-rays caused when the X-rays pass through the object. Many studies have been made on the scattered X-rays, aiming at their effective elimination. The complicated phenomena of the scattered X-rays impede or almost reject a theoretical approach to this theme. This is the present stage of technology in this field.

SUMMARY OF THE INVENTION

For the above background reasons, an object of the present invention is to provide, by introducing a novel technical idea, an X-ray diagnostic apparatus which can effectively eliminate the scattered X-ray image components from the transmitted X-ray image components as obtained by the X-ray detector.

The object of the present invention may be accomplished by providing an X-ray diagnostic apparatus comprising an X-ray source for successively generating X-rays, a detector for detecting an X-ray image of an object under examination by projecting the X-rays from the X-ray source toward the object, and for converting the detected image into first X-ray transmission signals including primary and scattered X-ray components, an analogue-to-digital converter for converting the first X-ray transmission signals into corresponding digital transmission data, an X-ray shield device positioned between the X-ray source and the detector and including a plurality of different X-ray shield pattern members for partially blocking the penetration of the X-rays over an X-ray projection area defined by projecting the X-rays from the X-ray source to the X-ray detector through the object, first memory means for storing at least first X-ray transmission data acquired during a first X-ray projection period under the condition that no X-ray shield pattern member has been inserted into the X-ray projection area, second memory means for storing at least second X-ray transmission data acquired during a second X-ray projection period under the condition that one of the X-ray shield pattern members has been inserted into the X-ray projection area, first arithmetic operation means for obtaining data representative of an intensity distribution of the scattered X-ray components, based upon the second transmission data, over the entire X-ray projection area by way of a linear interpolation method, second arithmetic operation means for subtracting the data representative of the intensity distribution of scattered X-ray components from the first transmission data so as to derive third transmission data from which the scattered X-ray components have been eliminated, a digital-to-analogue converter for converting the third transmission data into corresponding transmission signals, and means for displaying an X-ray transmission image, unaffected by the adverse influence of the scattered X-ray components by processing the transmission signals.

BRIEF DESCRIPTION OF THE DRAWINGS

This and other objects and features of the present invention may be best understood by reference to the specification and the accompanying drawings, in which;

FIGS. 3A, 3B and 3C graphically illustrate a spatial distribution of the scattered X-rays' intensity;

DETAILED DESCRIPTION OF THE PREFERRED EMBODIMENTS

Before proceeding with the various types of preferred embodiments according to the present invention, the principle of the present invention will now be described in detail.

First, a description is made of a phenomenon of the scattered X-ray.

It is assumed that X-rays incident on an object, such as a patient, under examination are generally classified into primary X-rays which directly transmit through the object and enter into an X-ray detector, and X-rays absorbed and/or scattered by the object through interactions of the X-rays with atoms constituting the object. Those scattered ones are called "scattered X-rays". In the energy range of medical X-rays (radiated under 50 KVp to 120 KVp of the X-ray tube voltage), some causes for the scattered X-rays are known, for example, photoelectric effects, Compton effects, Thomson effects, and the like. These phenomena cooperate to cause the scattered X-rays to have adverse effects on the transmitted X-ray image to be described later. In general, because the scattered X-rays incident on the X-ray detector experience multi-scattering within the object, it is very difficult to exactly grasp an intensity and a spatial spread of an incident X-ray beam. This phenomenon is explained as follows.

Figure 1:
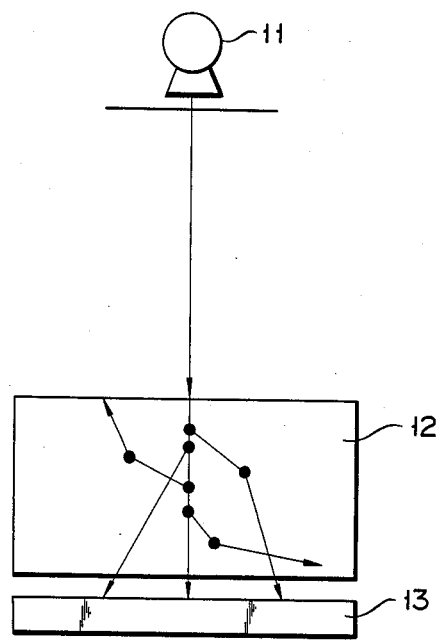
FIG. 1 is an illustration for explaining an occurrence of scattered X-rays when an X-ray is projected toward an object under examination.
Figure 2:
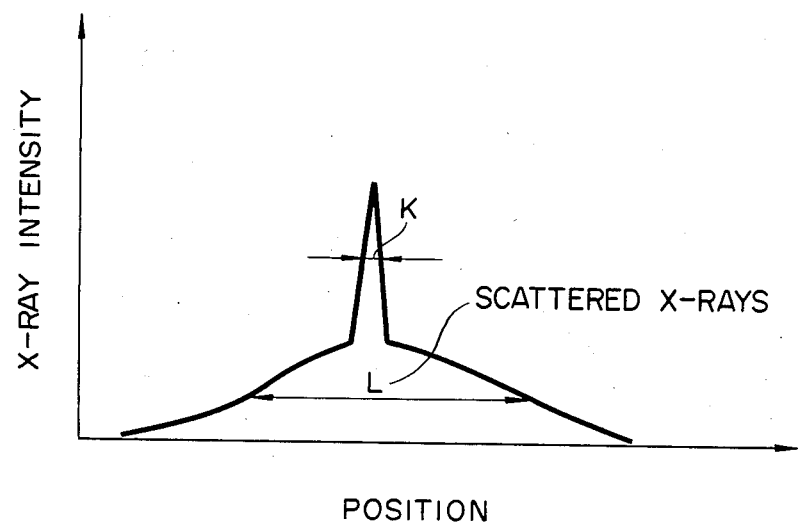
FIG. 2 shows a graphic representation of X-ray intensity vs. a detection position on an X-ray detector.

FIG. 1 schematically illustrates how an X-ray radiated from an X-ray source 11, such as an X-ray tube, is scattered within an object 12 under examination and reaches an X-ray detector 13, while depicting a spatial spread with respect to detecting positions of the X-ray detector. FIG. 2 illustrates an X-ray intensity distribution over the detecting positions of the X-ray detector 13. As seen from FIG. 2, a narrow spread, or spatial distribution of a sharp peak (as indicated by character "K"), located near the center of the distribution curve, is caused by an inherent matter of the diagnosis system, for example, an X-ray focal spot, and a wide spread (as indicated by character "L") is caused by the scattered X-rays.

In FIG. 3, a spatial distribution of the scattered X-rays is graphically shown. In FIG. 3A, a narrow X-ray beam is projected toward a body 14. In FIG. 3B, spatial distributions of the respective scattered X-rays are graphically shown. In FIG. 3C, an actual spatial distribution of the scattered X-rays is graphically shown, that is obtained by summing these spatial distributions. The characters "-a" and "a" define an area projected by the X-rays (referred to as an "X-ray projection area" hereinafter) on the detecting positions of the X-ray detector 13. The symbol "$I_{sc}(x)$" denotes an intensity of the scattered X-rays. For convenience and clarity of illumination, these drawings are illustrated in one dimension.

A total X-ray intensity distribution $I_m(x, y)$ incident on the detector 13 is the sum of the primary X-ray intensity distribution $I_p(x, y)$ and the scattered X-ray intensity distribution $I_{sc}(x, y)$ and is given by:

$$I_m(x, y) = I_p(x, y) + I_{sc}(x, y) \quad (1),$$

where (x, y) indicates coordinates for representing positions on the X-ray detector 13.

As previously described, since the spatial distributions of the scattered X-ray component $I_{sc}(x, y)$ gradually change over the X-ray projection area, it is possible to precisely recognize the scattered X-ray component, $I_{sc}(x, y)$ over the X-ray projection area by employing a plurality of the scattered X-ray component data in mathematical formula.

The basic embodiment of the present invention will now be briefly described based upon the above-identified recognition.

In accordance with the present invention, first transmitted X-ray image data (i.e., $I_m(x,y)$) is acquired under the condition that no X-ray shield member is interposed between the X-ray source and an X-ray detector within the X-ray projetion area. This image data contains scattered X-ray components and primary X-ray components. Next, the X-ray is projected toward an object under examination in such a way that an X-ray shield member (to be described in detail) is interposed between an X-ray source and an X-ray detector within the X-ray projection area. An X-ray projection area is defined by successively projecting the X-rays from the X-ray source to the X-ray detector through the object. Under such a condition, second transmitted X-ray image data (i.e., $I_{sc}(x, y)$) obtained by the detector may contain theoretically the scattered X-ray components only, because the primary X-ray components have been shielded by the X-ray shield member before reaching the X-ray detector. As a result, subtracting the second image data $I_{sc}(x, y)$ from the first image data $I_m(x, y)$ enables desirable image data $I_p(x, y)$ to be calculated in accordance with equation (1). This desirable image data involves only the primary X-ray components.

Figure 4:
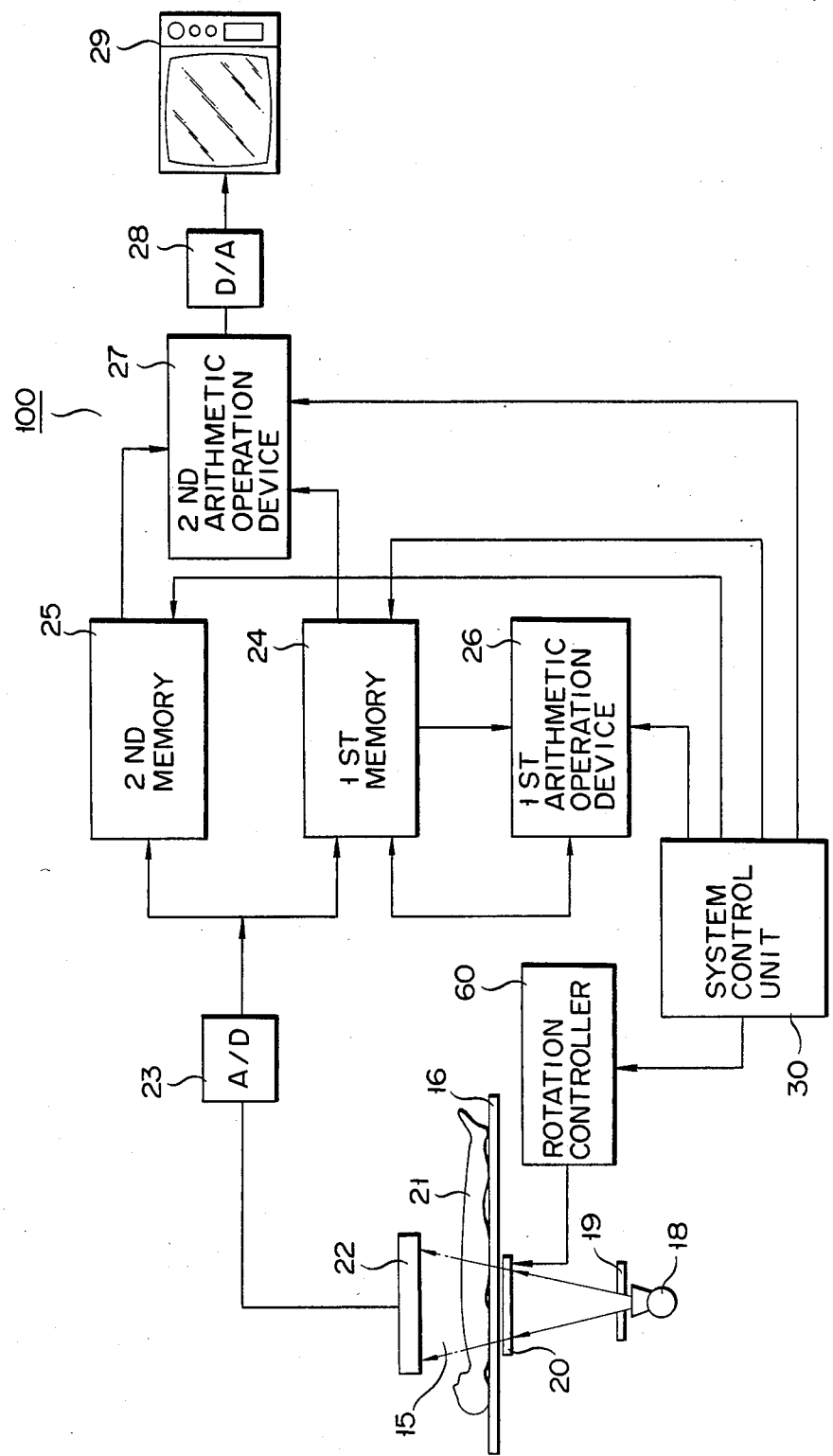
FIG. 4 shows a schematic block diagram of an X-ray diagnostic apparatus according to one preferred embodiment.

Referring to FIG. 4, a description is made of an X-ray diagnostic apparatus 100 according to the invention, in which the above basic idea is employed. An X-ray source 18 successively generates X-rays that are projected through an X-ray diaphragm 19 toward a patient 21 under examination. The patient 21 lies down on a couch 16. An X-ray projection area of the X-ray source 18 is denoted by reference numeral 15, that is defined by projecting the X-rays from the X-ray source 18 to the X-ray detector 22 through the patient 21.

An X-ray shield device 20 is provided under the couch 16. In other words, it is positioned in front of the patient 21 along the X-ray transmission path. This shield device 20 is designed to be rotatable with respect to a region of interest of the patient 21, or the X-ray projection area 15. The rotation operation into the X-ray projection area 15 will be described later.

A system control unit 30 is provided with the X-ray diagnostic apparatus 100. A rotation controller 60 can mechanically insert the X-ray shield member 20 within the X-ray projection area 15 under the control of the system control unit 30. An X-ray detector 22 is positioned behind the patient 21 along the X-ray transmission path within the X-ray projection area 15. Outputs of the detector 22 are fed to an analogue-to-digital converter (A/D converter) 23. To the A/D converter 23, first and second memories 24 and 25 are connected. The first memory 24 is communicated with a first arithmetic operation device 26 and the second memory 25 is communicated with a second arithmetic operation device 27. These first and second memories 24, 25, and first and second arithmetic operation devices 26, 27 are controlled by the system control unit 30. Outputs of the second arithmetic operation device 27 are fed to a digital-to-analogue converter (D/A converter) 28. The D/A converter 28 is connected to a TV monitor 29.

A detailed description will now be made of the X-ray shield device 20 with reference to FIGS. 5 and 6.

Figure 5:
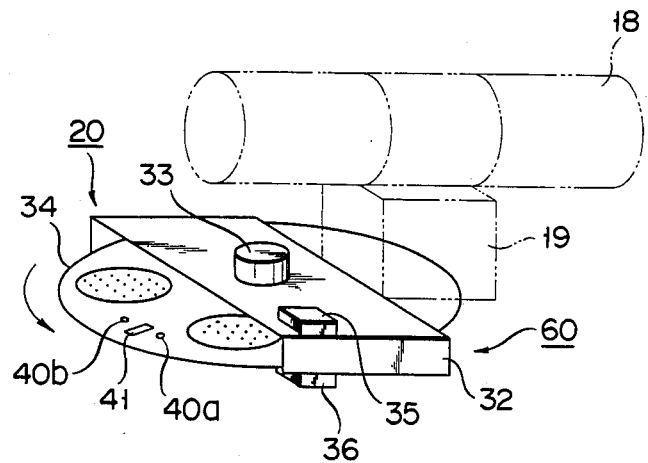
FIG. 5 is an illustration of the X-ray shield plate supporting member of FIG. 4.

FIG. 5 is a perspective view of the X-ray shield means 20 in combination with the rotation controller 60. FIG. 6 shows X-ray shield plates and a shield plate supporting member.

As shown in FIG. 5, the X-ray shield device 20 comprises a base 32 arranged adjacent to the X-ray diaphragm 19, a stepping motor 33 fixed to a central portion of the base 32, a shield plate supporting member 34, axially supported by a shaft (not shown) of the motor 33, on which a plurality of X-ray shield plates, to be described later, will be mounted, and both a light emitting element 35 and a light receiving element 36 for detecting first circular slits 40a and 40b and a second elongate slit 41 provided at a peripheral edge of the member 34 so as to align the X-ray shield plates mounted on the member 34.

It should be understood that the rotation controller 60 is constituted by the above-mentioned stepping motor 33, light emitting element 35, light receiving element 36 and base 32. Under control of the system control unit 30, the appropriate shield plate is inserted into the X-ray projection area 15 by the rotation controller 60.

Figure 6:
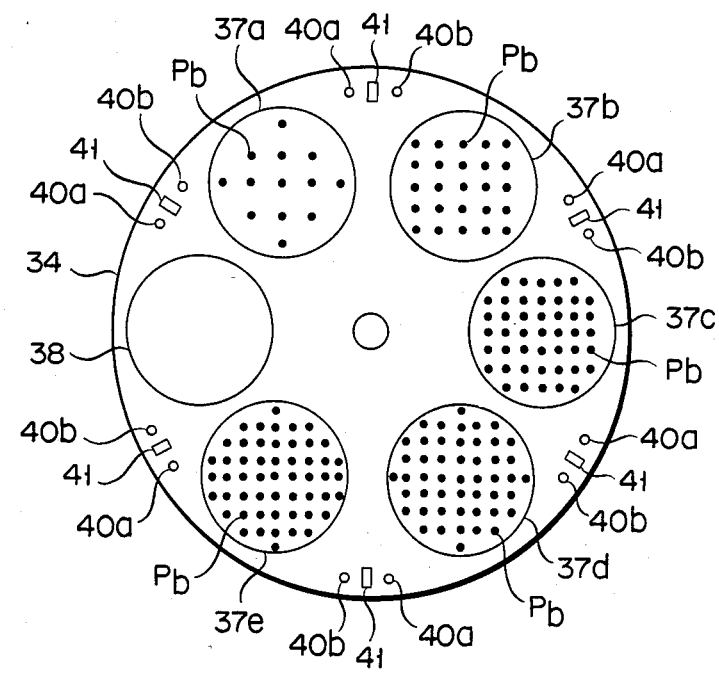
FIG. 6 is a plan view of the supporting member on which X-ray shield plates are mounted.

As shown in FIG. 6, the member 34 has a disk shape and is provided with a plurality of circular notch portions along a circumferential direction thereof. A plurality of X-ray shield plates 37a, 37b, 37c, 37d and 37e, having different X-ray shield patterns, are held by these circular notch portions.

Note that a portion indicated by reference numeral 38 can be either a notch portion or can support an X-ray transmission member constituting an X-ray shield plate (to be described later). In this sense, the portion indicated by reference numeral 38 will be called a vacancy 38 hereinafter.

The plates 37a to 37e constitute different X-ray shield patterns in such a manner that a plurality of X-ray shield members, e.g., 2 mm×2 mm lead pieces Pb are arranged on a circular X-ray transmission member, e.g., a synthetic resin film. The X-ray shield patterns are different for each X-ray shield plate, and correspond to X-ray diagnostic modes (to be described later).

It should be noted that one of the X-ray shield plates 37a to 37e and the vacancy 38 are successively selected in accordance with the X-ray diagnostic mode set by an operator, and that the selected one is loaded immediately under the X-ray projection area 15 or the X-ray diaphragm 19, i.e., over the region of interest of the patient 21. This operation can be made in such a manner that the number of slits passing between the elements 35 and 36 are counted; the operation of the motor 33 being controlled in accordance with the count result. The count of the number of slits and the operation control of the stepping motor are performed by the rotation controller 60 (FIG. 4).

The principle operation will be briefly described prior to a detailed description of the overall operation of the diagnostic apparatus according to the embodiment of the present invention.

First, a region of interest (ROI) of the patient 21 is determined. That is, ROI magnifying power for a desired X-ray diagnosis is determined. In other words, one of the shield plates 37a to 37e is selected so that a distance between images of the lead pieces Pb becomes constant when the X-ray shield pattern is projected on an effective light receiving surface of the detector 22 (normally a pick-up tube opposing an output surface of an image intensifier tube).

Second X-ray transmission data is then obtained. As described above, this data is data $I_{sc}(x, y)$, constituted only by scattered X-ray components. The shield plate used in the previous data acquisition is rotated by the rotation controller 60 so as to set the vacancy 38 in the projection area 15. The X-ray transmission data obtained in this state corresponds to the above-mentioned $I_m(x, y)$.

Thus, subtraction is made between the above two transmission data so as to obtain X-ray transmission data $I_p(x, y)$, constituted by a desired X-ray component.

The overall operation of the apparatus with the above arrangement and according to the embodiment will be described hereinafter.

One of the plates 37a to 37e, e.g., the plate 37b is selected in accordance with the X-ray diagnostic mode selected by the operator, e.g., a size of the detector 22 and a distance (i.e., magnifying power) between the X-ray source 18 and the patient 21, and the selected plate is loaded immediately under the X-ray diaphragm 19, i.e., in the X-ray projection area 15. In this state, the X-ray generated from the source 18 is partially shielded by the lead pieces of the plate 37b loaded in the area 15, and the X-ray transmitted through the plate 37b is radiated on the patient 21. The X-ray transmitted through the patient 21 is detected by the detector 22 as patient X-ray transmission data. The data is supplied to the A/D converter 23 for conversion into a digital signal, and the digital signal is temporarily stored in the first memory 24. The first arithmetic operation device 26 calculates scattered X-ray intensities in accordance with the data temporarily stored in the memory 24. That is, interpolation is performed in accordance with the transmission data corresponding to the portions covered by the lead pieces Pb, thereby calculating the scattered X-ray intensities of respective pixels.

The interpolation will be described with reference to FIGS. 7 to 9.

Figure 7:
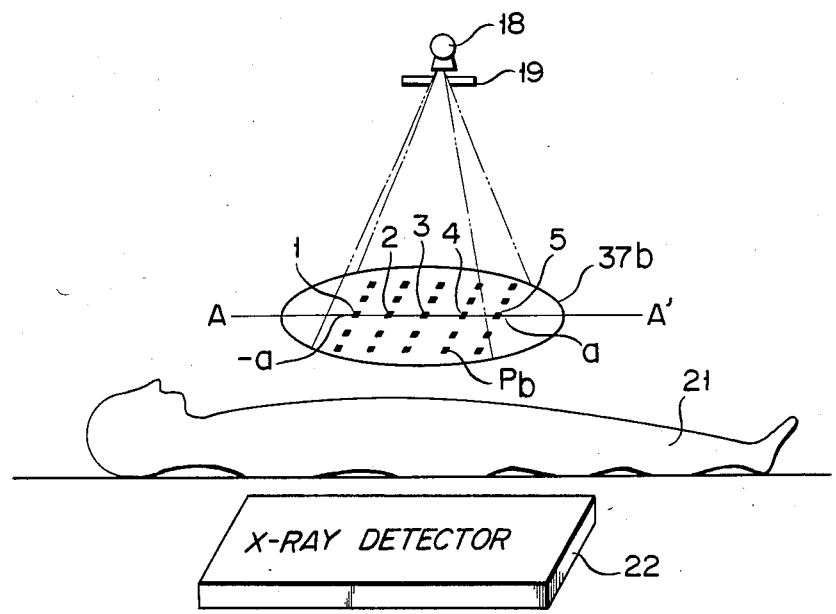
FIG. 7 is an illustration for explaining related positions between the X-ray source and the detector.
Figure 8:
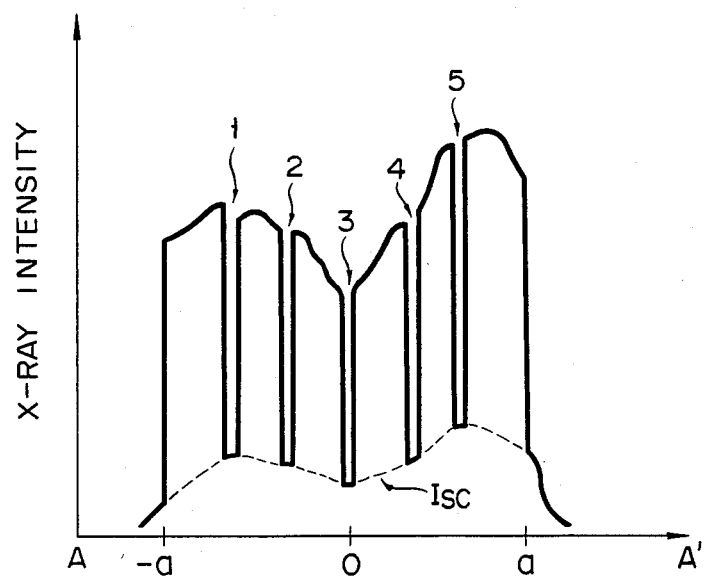
FIG. 8 shows a graphic representation of the relation between the X-ray intensity and the X-ray detecting area.

FIG. 7 is an illustration explaining X-ray radiation when the X-ray shield plate 37b is loaded in the X-ray projection area 15; FIG. 8 is a graph showing an X-ray intensity distribution at a position above the detector corresponding to a line A—A' of FIG. 7; and FIG. 9 is a graph explaining a method of interpolating the scattered X-rays.

It is assumed that, as shown in FIG. 7, the plate 37b is loaded in the area 15, and the X-rays transmitted through the plate 37b are radiated on the patient 21. In the X-ray intensity distribution obtained in this case at a position of the detector 22 corresponding to the line A—A' of FIG. 7, the intensities drop steeply at portions at which the X-rays are shielded by the lead pieces Pb, i.e., portions indicated by reference numerals 1, 2, 3, 4 and 5 as shown in FIG. 8. Values for the portions 1 to 5 represent the scattered X-ray intensities $I_{sc}$. Since the direct X-ray components $I_p$ are not present due to shielding by the lead pieces Pb, components distributed at the portions 1 to 5 cannot be other than scattered X-ray components. Thus, as shown in FIG. 9, the device 26 performs linear interpolation in accordance with the X-ray intensity distribution shown in FIG. 8.

Figure 9:
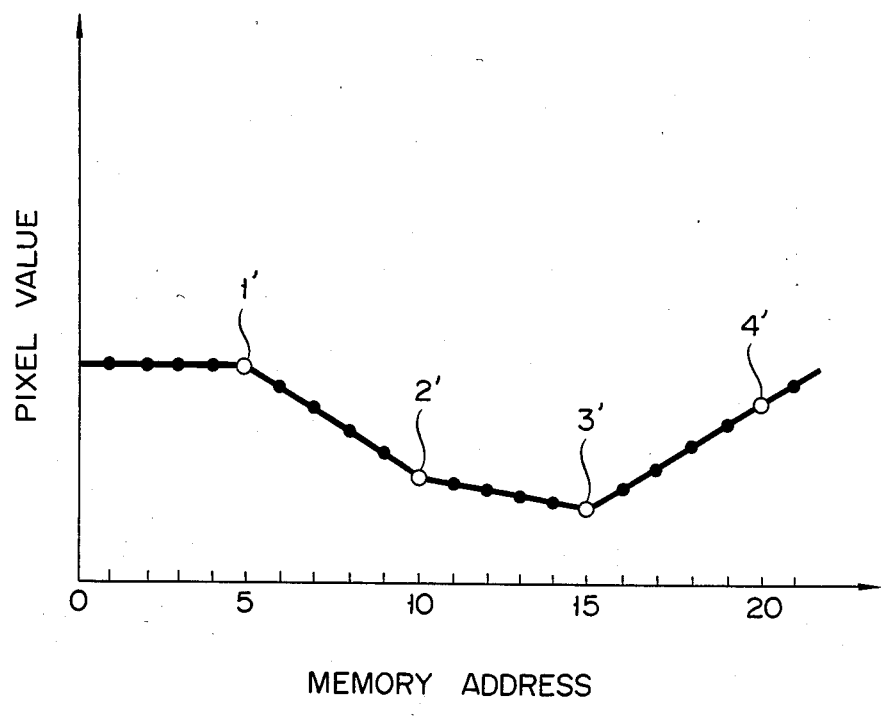
FIG. 9 schematically shows the linear interpolation method employed in the embodiment of FIG. 4.

The abscissa of FIG. 9 indicates memory addresses in the memory 24 corresponding to the line A—A' (FIG. 7), and the ordinate thereof indicates pixel values. In addition, circled values 1', 2', 3' and 4' correspond to 1, 2, 3 and 4 of FIG. 8, and indicate scattered X-ray intensity data measured in practice. Interpolated values of pixels obtained based upon the scattered X-ray data 1', 2', 3' and 4' are represented by dots. Note that since values to the left of the data 1' on the graph cannot be interpolated, i.e., measurement values required for interpolation cannot be obtained, the value of, e.g., the data 1' can be substituted. In this manner, the interpolated scattered X-ray data of all the total pixels on the line A—A' of the area 15 are stored in the memory 24 again. Furthermore, the same data acquisition and interpolation are performed for other lines, and the interpolated scattered X-ray data of the total area 15 are stored in the memory 24.

The motor 33 of the controller 60 is pivoted under the control of the unit 30, and the vacancy 38 is loaded in the area 15. In this state, the X-rays are radiated on the patient 21 from the source 18.

It should be noted that since the X-rays are radiated through the vacancy 38, the X-rays from the source 18 are radiated on the patient 21 without being partially shielded by the lead pieces. In this case, no X-ray shield plate is associated with the X-ray radiation. X-ray transmission data including primary and scattered X-ray components can be obtained. The X-ray transmission data obtained by this X-ray radiation is detected by the detector 22, and is converted into a digital signal by the A/D converter 23. Thereafter, the digital signal is stored in the second memory 25. In this manner, the X-ray intensity data acquisition is performed for the overall area 15. The data $I_m(x, y)$ stored in the memory 25, and the scattered X-ray data $I_{sc}(x, y)$ stored in the memory 24 are read out, and are subjected to calculation of equation (1) by the second arithmetic operation device 27. The device 27 subtracts the storage data (i.e., the scattered X-ray data $I_{sc}$) in the memory 24 from the storage data (i.e., the X-ray transmission data $I_m$ obtained when the X-ray shield plate is not associated) in the memory 25, and supplies the direct X-ray component data $I_p(x, y)$ (i.e., data excluding the scattered X-ray components) to the D/A converter 28. The input data is converted into an analogue signal from which the scattered X-ray components are removed, and is then subjected to X-ray image display on the monitor 29.

Figure 10A:
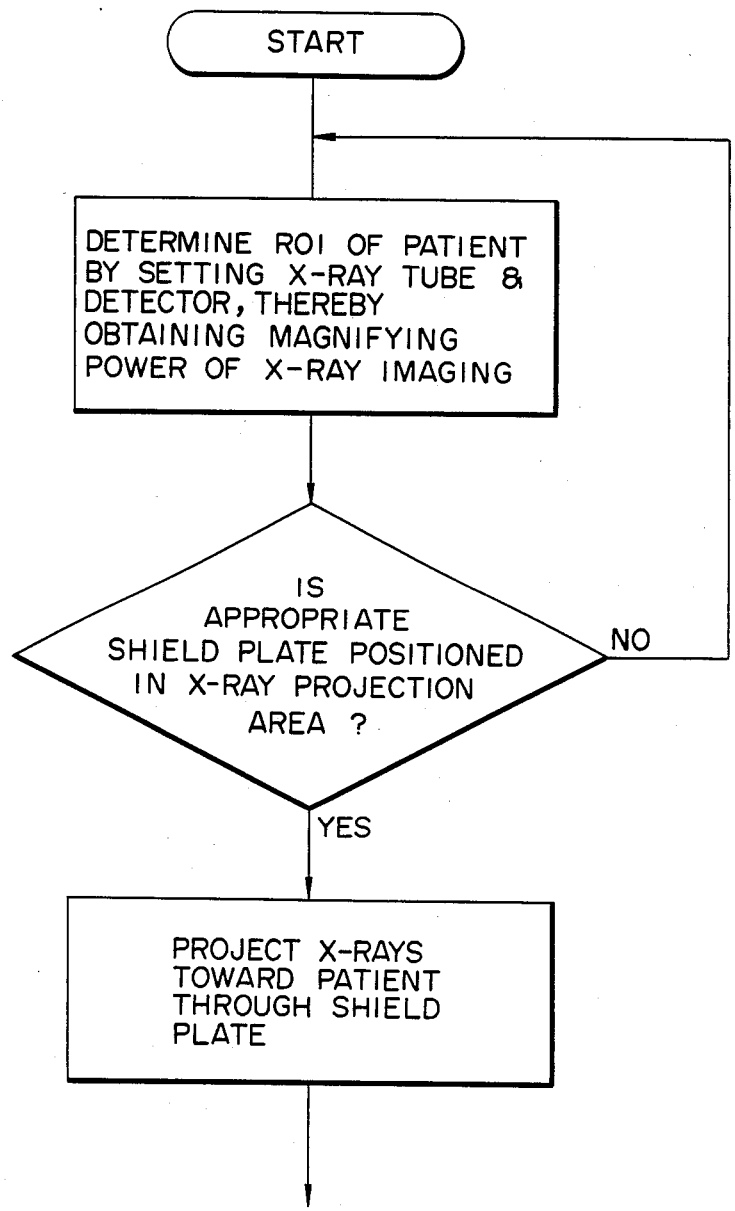
FIGS. 10A to 10C show a flow chart of typical operations of the first embodiment.
Figure 10B:
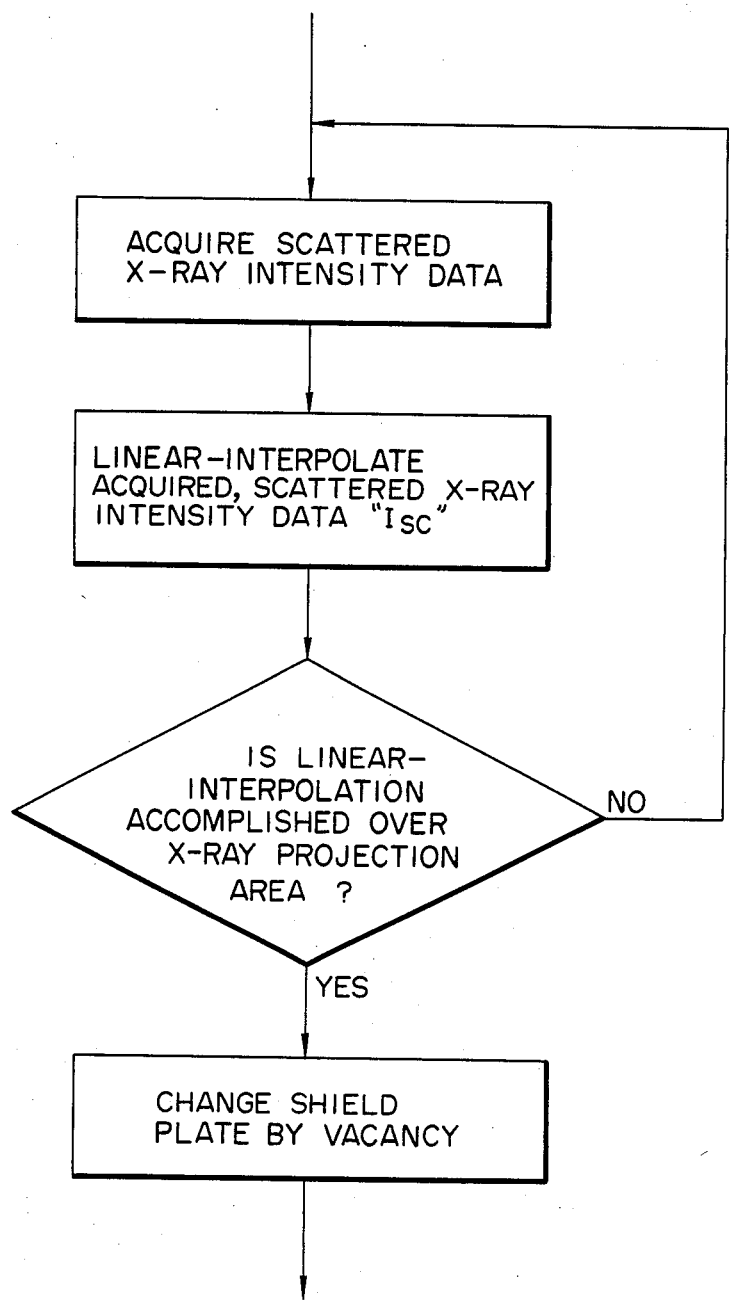
Figure 10C:
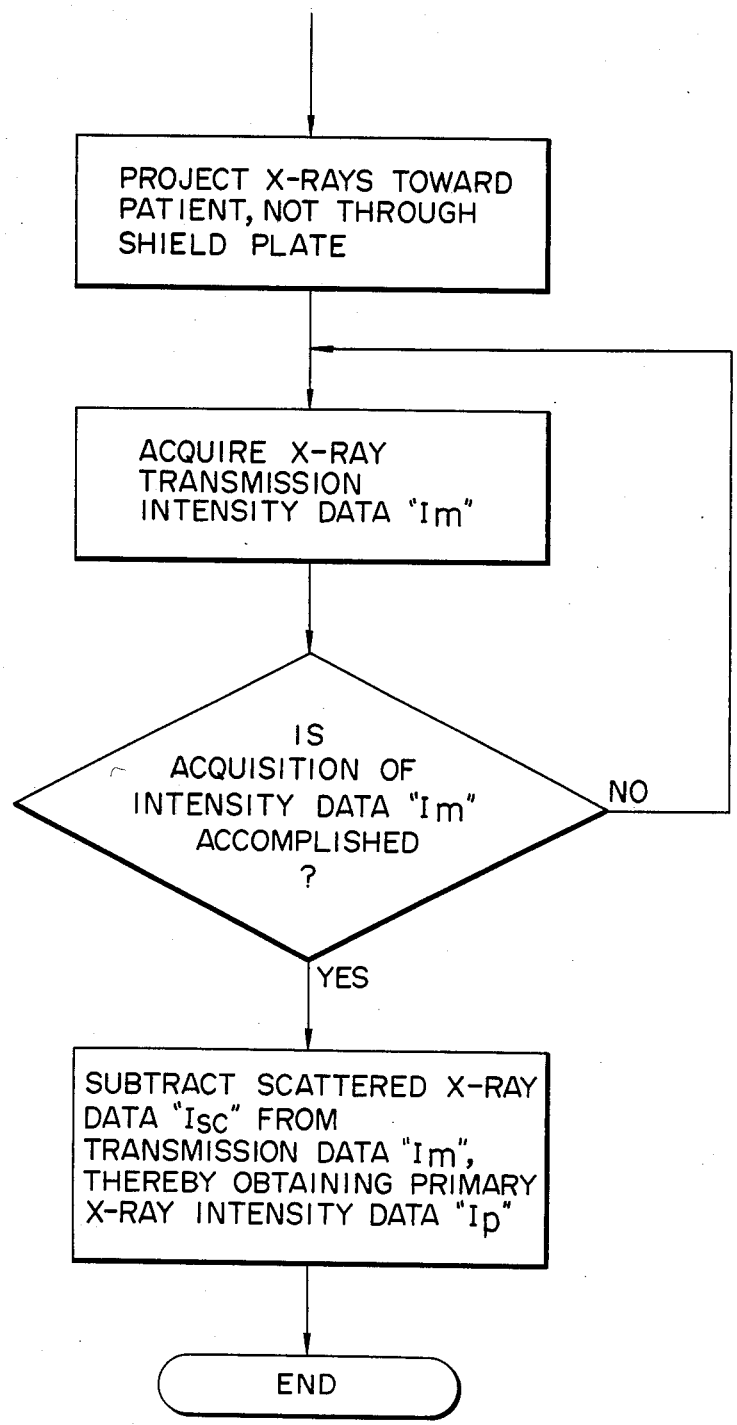

In FIG. 10, there is shown a flow chart of essential operations of the first embodiment which has been described in detail with reference to FIGS. 4 through 9.

The method of the linear interpolation employed in the previous apparatus 100 is described in detail in the co-pending U.S. patent application Ser. No. 673,792 (filed on Nov. 21, 1984).

According to the invention, many other interpolation methods can be utilized, for instance the SINC function interpolation which is also described in detail in the co-pending U.S. patent application Ser. No. 719,168 (filed on Apr. 2, 1985).

Features of our invention will now be summarized. A distance between, e.g., the X-ray source 18 and the detector 22 may be changed in accordance with examination modes. In this case, if X-ray imaging is performed without changing the X-ray shield pattern, the X-ray shield state on the surface of the detector 22 according to the lead pieces Pb, i.e., the points for measuring scattered X-ray component data or intervals of small regions is changed for every examination mode. As a result, an algorithm in the devices 26 and 27 for removing the scattered X-ray components must be altered.

In the present invention, the X-ray shield plate is selected based upon the X-ray diagnostic mode, and the the X-ray shield state on the surface of the detector 22 according to the lead pieces Pb is kept constant irrespective of a change in X-ray diagnostic modes. A complex algorithm for calculating scattered X-ray compensation in the devices 26 and 27 need not be changed, resulting in advantages in both hardware and software.

The loading operation of the X-ray shield plates under the control of the system control unit 30 and the rotation controller 60 will be described in detail. As shown in FIG. 6, when the second elongate slit 41 is provided between the first circular slits 40a and 40b formed in the peripheral edge of the member 34, the slit 40a or 40b passes between the elements 35 and 36 prior to the slit 41 and irrespective of the pivotal direction of the member 34. The unit 30 continuously monitors a current position of the member 34, and pivots the member 34 at high speed by the motor 33 of the controller 60 until the predetermined number of slits corresponding to the selected X-ray shield plate or the vacancy 38 have been counted. When the slit 40a or 40b (decided by the pivotal direction) is detected, the unit 30 decelerates the member 34 and stops it upon detection of the slit 41. In this manner, when the rotation of the member 34 is controlled, either the selected X-ray shield plate or the vacancy 38 can be quickly loaded in the X-ray projection area. Furthermore, since the member 34 is rotated at high speed and stopped smoothly through a gradual deceleration, the apparatus 100 causes the patient no discomfort.

The above-mentioned supporting member 34 is designed so that the vacancy 38 is always inserted in the area 15. More specifically, since the X-ray transmission intensity data is required in order to satisfy equation (1) to remove scattered X-rays, the program of the system control unit 30 is designed so as to always insert the vacancy 38 in the area 15 in a reset or initial state.

Consequently, in the apparatus of this embodiment, since scattered X-ray components can be removed and an X-ray image constituted only by the direct X-ray components can be displayed, a sharp, high contrast X-ray image of the object can be obtained without fading. The apparatus comprises a plurality of X-ray shield plates having different X-ray shield patterns, and is designed such that an X-ray shield plate can be automatically loaded in the X-ray projection area in accordance with the selected X-ray diagnostic mode. The apparatus can be compact in size in terms both of hardware and software, and a desired X-ray image can be obtained in a short period of time as compared with an apparatus in which shield plates are automatic function operated.

Although the present invention has been described with reference to its particular embodiment, the present invention is not limited to this. Various changes and modifications may be made within the spirit and scope of the invention. Another embodiment of the present invention will be described with reference to FIGS. 11 and 12.

Figure 11:
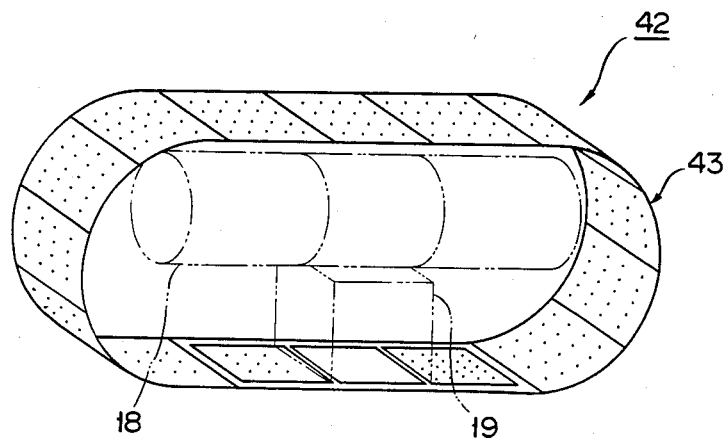
FIG. 11 is an illustration of X-ray shield plate supporting means according to another embodiment.
Figure 12:
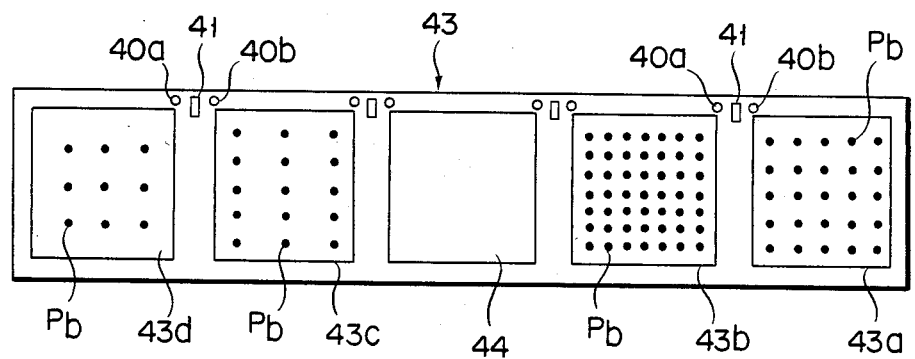
FIG. 12 is an illustration of portions of the shield plate supporting means shown in FIG. 11.

FIG. 11 is a perspective view showing an X-ray shield device 42 according to another embodiment of the present invention, while FIG. 12 is a developed view showing an X-ray shield plate and a shield plate supporting member of the device 42 shown in FIG. 11.

As shown in FIG. 11, a shield plate supporting member 43 is formed in a belt shape so as to surround an X-ray source 18 and an X-ray diaphragm 19. As shown in FIG. 12, rectangular X-ray shield plates 43a to 43d are mounted on the member 43. Note that reference numeral 44 denotes a vacancy.

When the device 42 is constituted as described above, and the member 43 is pivoted by a drive means (not shown) including a stepping motor, a desired X-ray shield plate can be loaded in an X-ray projection area 15, thus providing the same effect as in the first embodiment.

Furthermore, whereas in the first embodiment the scattered X-ray data $I_{sc}$ is acquired first by using the X-ray shield plate, and the X-ray transmission data $I_m$ is acquired second without using the X-ray shield plate, in this, the second embodiment, only acquisition of the data $I_m$ without use of the X-ray shield plate needs be done to complete the operation of the device 26. Consequently, the total time from data acquisition, to X-ray image display is considerably shortened. It should be added, however, that, in the case of this second embodiment, either acquisition of data Im without the X-ray shield plate or acquisition of data $I_{sc}$ with the X-ray shield plate can be realized to complete the operation of the device 26.

In the above embodiment, the X-ray shield plate is positioned in front of the patient along the X-ray transmission path. However, the present invention is not limited to this, and the X-ray shield plate can be positioned behind the patient. In this case, since magnifying power on the light receiving surface of the detector is changed (as compared to the embodiment of FIG. 4), the shield patterns or algorithm must be altered.

As described above, according to the present invention, scattered X-ray components can be removed from X-ray components incident on the detector irrespective of the X-ray diagnostic mode. Therefore, an X-ray diagnostic apparatus which can display an X-ray image of high contrast and sharpness, and without fading can be provided, thus contributing to an improvement in the performance of medical diagnosis.

What is claimed is:

1. An X-ray diagnostic apparatus comprising:
    an X-ray source for successively generating X-rays;
    means for detecting an X-ray image of an object under examination by projecting the X-rays from the X-ray source toward the object to produce X-ray transmission signals including primary and scattered X-ray components;
    an analogue-to-digital converter for converting the X-ray transmission signals into corresponding digital transmission data;
    X-ray shield means, positioned between the X-ray source and the detecting means, and including a plurality of different X-ray shield pattern members, each having elements for partially blocking the penetration of the X-rays over an X-ray projection area defined by projecting the X-rays from the X-ray source to the X-ray detection means through the object;
    means for selecting any one of said different X-ray shield pattern members in accordance with a change in the ratio of a source-to-object distance and source-to-image distance and a particular diagnostic test being performed and for inserting the selected one of said different X-ray shield pattern members within the X-ray projection area;
    first memory means for storing at least first X-ray transmission data acquired during a first X-ray projection period under the condition that no X-ray shield pattern member has been inserted into the X-ray projection area;
    second memory means for storing at least second X-ray transmission data acquired during a second X-ray projection period under the condition that the selected one of the X-ray shield pattern members has been inserted into the X-ray projection area;
    first arithmetic operation means for obtaining data representative of an intensity distribution of the scattered X-ray components, based upon the second transmission data, over the entire X-ray projection area by way of a linear interpolation method;
    second arithmetic operation means for subtracting the data representative of the intensity distribution of the scattered X-ray components from the first transmission data so as to derive third transmission data from which the scattered X-ray components have been eliminated;
    a digital-to-analogue converter for converting the third transmission data into corresponding transmission signals; and
    means for displaying an X-ray transmission image, unaffected by the adverse influence of the scattered X-ray components by processing the transmission signals.

2. An apparatus as claimed in claim 1, further comprising means for selecting a proper X-ray shield pattern member from said plurality of different X-ray shield pattern members in accordance with a magnifying power of the X-ray image of the object in relation to the detecting means, and for inserting said proper X-ray shield pattern member into the X-ray projection area during the first X-ray projection period.

3. An apparatus as claimed in claim 1, wherein the X-ray shield pattern member is constructed of a synthetic resin film and a plurality of lead pieces positioned in a matrix.

4. An apparatus as claimed in claim 1, wherein the X-ray shield means is comprised of a circular holding plate on which at least said plurality of X-ray shield pattern members are mounted around the peripheral portion thereof and a plurality of position indicators are formed in combination with the respective X-ray shield pattern members.

5. An apparatus as claimed in claim 4, further comprising an X-ray transmission member mounted on the peripheral portion of the circular holding plate, and a plurality of position indicators formed in combination with the X-ray transmission member.

6. An apparatus as claimed in claim 4, wherein a plurality of through holes are formed in the circular holding plate so as to permit the X-rays to be transmitted therethrough.

7. An apparatus as claimed in claim 4, wherein said selecting means includes a pulse motor for rotating the circular holding plate, and an optical position sensor for detecting said proper X-ray shield pattern member by optically sensing the position indicators related thereto.

8. An apparatus as claimed in claim 7, wherein the position indicators include a rectangular slit and a first and second circular slit sandwiching the rectangular slit, and the optical position sensor is comprised of a light emitting element and a photoelectric sensor, wherein, at times when one of the circular slits passes between the light emitting elements and the photoelectric sensor, a speed of rotation of the shield pattern member is reduced and, at times when the rectangular slit passes between the light emitting elements and the photoelectric sensor, the speed of rotation is stopped.

9. An apparatus as claimed in claim 2, wherein the X-ray shield means is comprised of a holding belt on which at least said plurality of X-ray shield pattern members are mounted side by side, and a plurality of position indicators are formed in combination with the respective X-ray shield pattern members.

10. An apparatus as claimed in claim 9, further comprising an X-ray transmission member mounted on the holding belt around the edge portion thereof, and a plurality of position indicators formed in combination with the X-ray transmission member.

11. An apparatus as claimed in claim 9, wherein a plurality of through holes are formed in the holding belt so as to permit the X-rays to be transmitted therethrough.

12. An apparatus as claimed in claim 9, wherein said selecting means includes a pulse motor for driving the holding belt, and an optical position sensor for detecting said proper X-ray shield pattern member by optically sensing the position indicators related thereto.

13. An apparatus as claimed in claim 12, wherein the position indicators include a rectangular slit and a first and second circular slit sandwiching the rectangular slit, and the optical position sensor is comprised of a light emitting element and a photoelectric sensor; wherein, at times when one of the circular slits passes between the light emitting element and the photoelectric sensor, a speed of rotation of the shield pattern member is reduced and, at times when the rectangular slit passes between the light emitting elements and the photoelectric sensor, the speed of rotation is stopped.

* * * * *